US010781287B2

(12) United States Patent
Hoogenboom et al.

(10) Patent No.: US 10,781,287 B2
(45) Date of Patent: Sep. 22, 2020

(54) METHOD FOR THE PREPARATION OF UNIFORM, HIGH MOLAR MASS CYCLIC IMINO ETHER POLYMERS

(71) Applicant: Universiteit Gent, Ghent (BE)

(72) Inventors: Richard Hoogenboom, Terneuzen (NL); Bryn Monnery, Ghent (BE)

(73) Assignee: UNIVERSITEIT GENT, Ghent (BE)

( * ) Notice: Subject to any disclaimer, the term of this patent is extended or adjusted under 35 U.S.C. 154(b) by 69 days.

(21) Appl. No.: 16/053,700

(22) Filed: Aug. 2, 2018

(65) Prior Publication Data

US 2018/0346649 A1   Dec. 6, 2018

Related U.S. Application Data

(62) Division of application No. 15/326,866, filed as application No. PCT/EP2015/065829 on Jul. 10, 2015, now Pat. No. 10,118,991.

(30) Foreign Application Priority Data

Jul. 18, 2014   (EP) .................................... 14177587

(51) Int. Cl.
*A61K 47/48*   (2006.01)
*C08L 79/02*   (2006.01)
(Continued)

(52) U.S. Cl.
CPC .......... *C08G 73/0233* (2013.01); *A61K 47/34* (2013.01); *A61K 47/59* (2017.08); *C08L 79/02* (2013.01)

(58) Field of Classification Search
CPC .................................................... A61K 47/48
(Continued)

(56) References Cited

U.S. PATENT DOCUMENTS 3,326,929 A   6/1967   Seeliger
4,281,137 A   7/1981   Sanner et al.
(Continued)

FOREIGN PATENT DOCUMENTS

EP   1 930 361 A1   6/2008
EP   2586815 A1   5/2013
(Continued)

OTHER PUBLICATIONS

Hoogenboom et al., "Concentration effects in the cationic ring-opening polymerization of 2-ethyl-2-oxazoline in N,N-dimethylacetamide", Journal of Polymer Science Part A: Polymer Chemistry, 2005, vol. 43, pp. 1487-1497.
(Continued)

*Primary Examiner* — Duc Truong
(74) *Attorney, Agent, or Firm* — Foley & Lardner LLP (57) ABSTRACT

A method for production of a uniform polymer of high molar mass is provides, the method comprising: (a) polymerizing cyclic imino ether monomer in a first reaction mixture by cationic ring opening polymerization to produce a polymerized first reaction mixture containing (i) polymerized material and (ii) solvent and/or unreacted cyclic imino ether monomer; (b) separating solvent and/or unreacted cyclic imino ether monomer from polymerized material contained in the polymerized first reaction mixture; (c) copolymerizing by cationic ring opening polymerization a second liquid reaction mixture containing cyclic imino ether monomer and solvent by combining the separated unreacted cyclic imino ether monomer and/or the separated solvent with other components. Also disclosed are polyoxazoline polymers comprising at least 50 wt. % of repeating units derived from a 2-substituted 2-oxazoline monomer selected from 2-methyl-2-oxazoline, 2-ethyl-2-oxazoline, 2-n-propyl-2-oxazoline, 2-i-propyl-2-oxazoline and combinations thereof,
(Continued)

said polymer having a DP of at least 250 and a very low dispersity.

8 Claims, 9 Drawing Sheets

(51) Int. Cl.
  *C08G 73/02* (2006.01)
  *A61K 47/59* (2017.01)
  *A61K 47/34* (2017.01)

(58) Field of Classification Search
  USPC .......................................................... 528/40
  See application file for complete search history.

(56) References Cited

U.S. PATENT DOCUMENTS

2009/0156782 A1  6/2009  Kataoka et al.
2010/0197888 A1  8/2010  Adib et al.

FOREIGN PATENT DOCUMENTS

WO   WO-2008/106186 A2   9/2008
WO   WO-2013/103297 A1   7/2013
WO   WO-2011/162366      8/2013

OTHER PUBLICATIONS

Viegas et al., "Polyoxazoline: Chemistry, properties, and applications in drug delivery", Bioconjugate Chemistry, 2011, vol. 22, pp. 976-986.
International Search Report issued in International Patent Application No. PCT/EP2015/065829 dated Aug. 26, 2015.

METHOD FOR THE PREPARATION OF UNIFORM, HIGH MOLAR MASS CYCLIC IMINO ETHER POLYMERS

CROSS-REFERENCE TO RELATED APPLICATIONS

This application is a divisional of U.S. patent application Ser. No. 15/326,866 filed Jan. 17, 2017 now U.S. Pat. No. 10,118,991, which is the National Phase of International Patent Application No. PCT/EP2015/065829 filed Jul. 10, 2015, published on Jan. 21, 2016 as WO 2016/008817 A1, which claims priority to European Patent Application No. 14177587.4 filed Jul. 18, 2014. The contents of these applications are herein incorporated by reference in their entirety.

TECHNICAL FIELD OF THE INVENTION

The invention relates to a method for the preparation of cyclic imino ether polymers having a high molar mass and a low (poly)dispersity and to polyoxazoline polymers having such properties. The invention relates further to pharmaceutical compositions and medical devices containing such polymers.

BACKGROUND OF THE INVENTION

The pharmaceutical and biotechnology industries face an important challenge of improving the therapeutic efficacy of drugs and drug-candidates. For the administration of certain types of pharmaceuticals conventional dosage forms are not always very suitable. For instance, many of the most potent drugs and drug candidates have a low solubility in water and are thus not adequately absorbed by the body; small drugs suffer from a fast renal clearance and biopharmaceuticals undergo rapid enzymatic degradation.

Various approaches have been used to improve the pharmacokinetic and pharmacodynamic properties of such drugs, one of them being conjugating the drug to natural or synthetic polymers and another one being the formation of solid dispersion and solid solutions using a polymer excipient.

Poly(ethylene glycol) (PEG) is most often used as a carrier for the conjugation of drugs. By increasing the molecular weight of a pharmaceutical through PEGylation, several significant pharmacological advantages over the unmodified form arise, such as an improved drug solubility, extended circulating half-life, reduced immunogenicity, increased drug stability and an improved protection against proteolytic degradation. PEG improves a drug's therapeutic efficacy by increasing the drug's hydrodynamic radius, thereby (partially) shielding it from interactions with the body, including the immune system and proteolytic enzymes. Especially this latter shielding property is the main driving force for the success of PEG, compared to many other water soluble polymers, which is believed to result form the good hydration of PEG.

Despite the common use of PEGylation there are several disadvantages associated with its use. Sometimes, hypersensitivity and the formation of PEG antibodies is observed. It is also observed that when PEG with high molecular weights is used, it accumulates in the liver, leading to the so called macromolecular syndrome. The chain length of the PEG molecules may be reduced under the influence of enzymes, such as P450 or alcoholdehydrogenase, giving rise to toxic side products.

With respect to small therapeutic molecules it is often observed that with PEG only a relatively low drug loading can be achieved due to the presence of merely one or two hydroxyl terminal groups that can be activated. Furthermore, orthogonal functionalization of PEG or PEG dendrons with the therapeutic moiety, detection moiety or targeting moiety is not readily possible.

Furthermore, it is relatively difficult and hazardous to prepare PEG as explosive and highly toxic condensed ethylene oxide monomers are required. In addition, PEG has a limited storeability, i.e. an antioxidant is required for storage in order to avoid peroxide formation.

Therefore, there is a need for well defined, non-immunogenic and non-toxic polymer carriers for drug delivery.

For fulfilling this purpose, polyoxazolines (PDX) seem to be promising candidates. They typically offer the advantages of a straightforward preparation, a good stability, a low toxicity and immunogenicity, large loading capacities, good hydrophilic properties and good protein repellent effects.

However, an important drawback of commercially available synthetic polymeric materials like PEG and PDX lies in the fact that they are not very uniform in that they comprise a broad mixture of polymers of various chain lengths. This heterogeneity of molecular weight ('polydispersity')—or 'dispersity' as nowadays recommended by the IUPAC)—is an inherent result of the polymer's production process. Small impurities in the reaction mixture cause side-reactions during polymerization that lead to preliminary chain termination.

It is readily understood that for biomedical applications it is highly desirable to employ well-defined, chemically homogeneous materials. As far as high molar mass polymers are concerned it is generally desirable to minimize the level of low molar mass polymer fragments. In other words, it is important to reduce the dispersity of polymers for biomedical applications as much as possible. This goal is particularly difficult to achieve, since biomedical applications usually require high molecular weight polymers and dispersity increases with increasing molar mass, especially for cyclic imino ether polymers as during preparation of these polymers intrinsic chain transfer occurs by so-called beta-elimination.

WO 2008/106186 describes a terminally activated polyoxazoline (PDX) compound comprising a PDX polymer having a single active functional group on a terminal end thereof, said functional group capable of reacting with a group on a target molecule to create a target molecule-PDX conjugate. In the international patent application it is observed that it is frequently necessary for commercial development of polymer-modified drugs to utilize polymers with molecular weights (MWs) as high as 40,000 Da or higher and with molecular weight distributions or polydispersities (PDs) of less than 1.1, but that there has been a great deal of work showing that MWs and PDs in the above range cannot be achieved for PDX with conventional techniques. WO 2008/106186 describes methods for obtaining PDX derivates with low PD values involving purification of the reaction mixture by anion exchange chromatography. Example 36 describes a polyethyloxazoline polymer with a MW of 15.200 Da and a PD of 1.09.

US 2009/156782 describes a method for preparing monodispersible homo- and random copolymers of 2-ethyl-2-oxazoline and 2-iso-propyl-2-oxazoline. The method described by US 2009/156782 involves dialysis purification of the reaction mixture against water. Referential example 1 describes the preparation of a poly(2-isopropyl-2-oxazoline)

polymer with a molecular weight ($M_n$) of 9700 (DP=86) and a degree of dispersion ($M_w/M_n$) 1.02.

U.S. Pat. No. 3,326,929 describes treating oxazoline monomers with acid chlorides or acid anhydrides in order to satisfactorily purify said oxazoline monomers so that polymerization can be effected by cation-active catalysts without chain breakage. The exact $M_n$ and dispersity of the resulting polymers are not reported.

U.S. Pat. No. 4,281,137 describes the removal of residual amounts of water and color-causing impurities from 2-oxazoline compounds for attenuating the undesirable effect of these impurities on the color of an oxazoline polymer. This is achieved by reacting the monomers with chlorosilanes or phosphites. The US patent does not contain any information on the $M_n$ and dispersity of the resulting polymers.

T. X. Viegas et al. (2011) *Bioconjugate Chem.* 22, 976-986 describes a specific procedure for the synthesis of 5 kDa and 10 kDa polyethyloxazoline polymer with a dispersity of less than 1.1.

SUMMARY OF THE INVENTION

The inventors have developed a method of producing a uniform polymer of high molar mass by cationic ring-opening polymerisation of a cyclic imino ether monomer. This method has the advantage that impurities are essentially completely removed from the reaction mixture, so that no significant side reactions take place during polymerization. Side-reactions are further suppressed by performing the polymerization at low temperatures. The present method can thus advantageously be used to produce a cyclic imino ether polymer of biomedical grade, having a high molar mass and narrow distribution of molecular weights (low dispersity).

The method according to the present invention comprises the following steps:
a) providing a first liquid reaction mixture comprising cyclic imino ether monomer and optionally solvent;
b) polymerizing cyclic imino ether monomer in the first reaction mixture by cationic ring opening polymerization to produce a polymerized first reaction mixture containing (i) polymerized material and (ii) solvent and/or unreacted cyclic imino ether monomer;
c) separating solvent and/or unreacted cyclic imino ether monomer from polymerized material contained in the polymerized first reaction mixture;
d) providing a second liquid reaction mixture containing cyclic imino ether monomer and solvent by combining the separated unreacted cyclic imino ether monomer and/or the separated solvent with other components (solvent, monomer and/or initiator); and
e) polymerizing the cyclic imino ether monomer in the second reaction mixture by cationic ring opening polymerization to produce a uniform polymer having a degree of polymerization (DP) of at least 100.

Although the inventors do not wish to be bound by theory, it is believed that contaminants that can cause preliminary termination of the polymerization reaction are effectively removed during steps a) to c) of the present method, thereby providing a second liquid reaction mixture that is essentially free of such contaminants. Thus, the second liquid reaction mixture can be polymerized to yield a high molar mass polymer of very low dispersity.

The present invention further relates to poly(2-oxazoline) polymers with a high molecular weight and low dispersity. More specifically, the present invention relates to a polymer comprising at least 50 wt. % of repeating units derived from a 2-substituted 2-oxazoline monomer selected from 2-methyl-2-oxazoline, 2-ethyl-2-oxazoline, 2-n-propyl-2-oxazoline, 2-i-propyl-2-oxazoline and combinations thereof, said polymer having a DP of at least 250 and a dispersity of less than $\theta_{max}$, wherein $\theta_{max}$ is calculated by the following equation:

$$\theta_{max}=1.2+(DP-250)/8000 \text{ when } 250 \leq DP < 900;$$

$$\theta_{max}=1.28125+(DP-900)/500 \text{ when } 900 \leq DP < 1000;$$

$$\theta_{max}=1.48125+(DP-1000)/9770 \text{ when } 1000 \leq DP.$$

The present invention further relates to pharmaceutical compositions or medical devices containing such polymer.

BRIEF DESCRIPTION OF THE FIGURES

HFIP SEC revealed a monomodal peak as narrow as the PMMA standards used to calibrate the columns as shown in FIG. 1, FIG. 2, FIG. 4, FIG. 5, FIG. 7, FIG. 8 and FIG. 9.

HFIP SEC revealed a monomodal peaks as narrow as the PMMA standards used to calibrate the column as shown in FIG. 3 for both the homopolymer and diblock copolymer.

HFIP SEC revealed both the homopolymer and the triblock to have monomodal peaks as narrow as the PMMA standards used to calibrate the column as shown in FIG. 6.

DETAILED DESCRIPTION OF THE INVENTION

Accordingly, one aspect of the invention relates to a method of producing a uniform polymer of high molar mass by cationic ring-opening polymerisation of a cyclic imino ether monomer with 5 or 6 ring members, said method comprising the following steps:
a) providing a first liquid reaction mixture comprising cyclic imino ether monomer and optionally solvent;
b) polymerizing cyclic imino ether monomer in the first reaction mixture by cationic ring opening polymerization to produce a polymerized first reaction mixture containing (i) polymerized material and (ii) solvent and/or unreacted cyclic imino ether monomer;
c) separating solvent and/or unreacted cyclic imino ether monomer from polymerized material contained in the polymerized first reaction mixture;
d) providing a second liquid reaction mixture containing cyclic imino ether monomer and solvent by combining the separated unreacted cyclic imino ether monomer and/or the separated solvent with other components; and
e) polymerizing the cyclic imino ether monomer in the second reaction mixture by cationic ring opening polymerization to produce a uniform polymer having a degree of polymerization (DP) of at least 100.

The term "cyclic imino ether" as used herein refers to a substituted or unsubstituted heterocyclic organic compound whose ring members include one atom of oxygen and one atom of nitrogen, separated by one carbon atom. Examples of cyclic imino ethers are oxazolines (containing a 5 membered ring) and oxazines (containing a 6 membered ring).

The term 'degree of polymerisation' as used herein, unless indicated otherwise, refers to the number-averaged degree of polymerization.

The term "dispersity" as used herein, unless indicated otherwise, refers to the dispersity index $\theta$. It can be calculated using the equation: $\theta_{DP}=M_w/M_n$, where $M_w$ is the weight-averaged molecular weight of the polymer and $M_n$ is the number-averaged molecular weight.

The term "chain breaking impurities" as used herein, unless indicated otherwise, refers to substances that are capable of causing preliminary termination or chain transfer reactions of the cationic ring opening polymerization of the cyclic imino ether monomer that is employed in the second reaction mixture.

The term "cryogenic distillation" as used herein refers to a distillation process in which vacuum is used to aid evaporation of volatiles from and in which these volatiles are condensed by cryogenic cooling.

The method according to the present invention can suitably be used to prepare high molar mass polymers from oxazolines, oxazines and other cyclic imino ethers. According to a preferred embodiment, the cyclic imino ether monomer employed in the present method is an optionally substituted oxazoline, preferably an optionally 2-substituted, 2-oxazoline.

Examples of 2-substituted, 2-oxazolines that can suitably be used as monomers in the present method include 2-methyl-2-oxazoline, 2-ethyl-2-oxazoline, 2-n-propyl-2-oxazoline, 2-i-propyl-2-oxazoline, 2-butyl-2-oxazoline, 2-(3-butenyl)-2-oxazoline, 2-(methoxycarboxyethyl)-2-oxazoline and combinations thereof.

The polymerization of the first reaction mixture is typically carried out at a temperature in the range of 0 to 100° C., preferably 10 to 60° C. and most preferably 30 to 50° C. The reaction can be carried out under vacuum or in an inert atmosphere.

The first reaction mixture should contain an amount of living polymer leading to oligomeric or polymeric living polymer chains in a sufficient quantity to react with all chain breaking impurities that are present. In the method according to the present invention, the first reaction mixture typically contains 10-100 wt. % of the cyclic ether monomer. Even more preferably the first reaction mixture contains 15-80 wt. %, most preferably 20-50 wt. % of the cyclic imino ether monomer.

The present method may suitably employ a first reaction mixture that is solvent-free. Preferably, the first reaction mixture contains 5-90 wt. % of solvent. More preferably, the solvent content of the first reaction mixture lies in the range of 20-80 wt. %, most preferably of 50-80 wt. %.

The inventors have found that non-interfering, unreactive solvents (either polar or apolar) are the most suitable media for carrying out the polymerization of the first reaction mixture. In the method according to the invention, the solvent in the first reaction mixture is preferably selected from optionally substituted aromatic hydrocarbons, sulfolane, dimethylacetamide and mixtures thereof. More preferably, said solvent is, the solvent is an optionally substituted aromatic hydrocarbon, most preferably chlorobenzene.

In order to ensure that the actual polymerization step carried out in the second reaction mixture is not hindered by dispersity-increasing side reactions, it is important that during the sacrificial polymerization in the first reaction mixture all of the chain breaking impurities react with the living poly(cyclic imino ether) chains. To achieve this it is useful to include a polymerization initiator in the first reaction mixture. Typically, the first reaction mixture contains an initiator in a concentration of 0.1-10 wt. %, more preferably of 0.5-5 wt. % and most preferably of 1-2 wt. %.

The sacrificial polymerization in the first reaction mixture yields polymerized material. The remaining solvent and/or unreacted cyclic imino ether monomer are essentially completely free from chain breaking impurities and need to be separated from the polymerization material before they can be used in the second polymerization step.

In a preferred embodiment of the present invention the solvent and/or unreacted cyclic imino ether monomer is separated from polymerized material contained in the polymerized first reaction mixture by means of distillation, preferably by means of cryogenic distillation.

The separated solvent and the separated unreacted cyclic imino ether monomer that are obtained from step c) of the present method are both essentially completely free from chain breaking impurities. The benefits of the present invention may be realized by including either the separated solvent or the separated monomer in the second liquid reaction mixture. Naturally, these same benefits are also realized if both the separated solvent and the separated monomer are employed in the second reaction mixture.

According to one embodiment of the method of the present invention, the solvent separated from polymerized material contained in the polymerized first reaction mixture is subsequently combined with cyclic imino ether monomer to produce the second liquid reaction mixture.

In order to minimize the concentration of chain breaking impurities in the separated solvent, it is important that the solvent is separated from the polymerized material in such a way that it contains virtually no polymerized material. Preferably, the separated solvent comprises less than 10 ppm, more preferably less than 5 ppm, and even more preferably less than 1 ppm of polymerized material. Most preferably, the separated solvent contains no polymerized material.

In another preferred embodiment of the present method, before separation of the solvent from polymerized material in step c), additional solvent is added to the first liquid reaction mixture after at least 95 wt. % of the cyclic imino ether monomer has polymerized, followed by continuation of the cationic ring opening polymerization, the additional solvent representing more than 80 wt. % of the solvent employed in the first liquid reaction mixture. This embodiment offers the advantage that the efficiency of the sacrificial polymerization step is increased significantly, due to the fact that the initial polymerization rates are substantially higher than in case all solvent is introduced into the first reaction mixture before the start of the polymerization.

According to another embodiment of the present method, the unreacted cyclic imino ether monomer is separated from polymerized material contained in the polymerized first reaction mixture and subsequently the separated unreached cyclic imino ether monomer is combined with solvent to produce the second liquid reaction mixture.

In order to minimize the concentration of chain breaking impurities in the separated monomer the unreacted cyclic imino ether monomer should be separated from the polymerized material in such way that it contains virtually no polymerized material. Preferably, the separated unreacted cyclic imino ether comprises less than 10 ppm, more preferably less than 5 ppm and even more preferably less than 1 ppm of polymerized material. Most preferably, the separated unreacted cyclic imino ether monomer comprises no polymerized material.

In accordance with a particularly preferred embodiment of the method of the present invention, both the separated solvent and the separated unreacted cyclic imino ether monomer are combined with other components to produce the second liquid reaction mixture.

In yet another embodiment of the present method solvent and unreacted cyclic imino ether monomer are separated from polymerized material contained in the polymerized first reaction mixture and combined with other components to produce the second liquid reaction mixture. In order to minimize the concentration of chain breaking impurities in the separated monomer the solvent and unreacted cyclic imino ether monomer should be separated from the polymerized material in such way that it contains virtually no polymerized material. Preferably, the separated combination of solvent and unreacted cyclic imino ether comprises less than 10 ppm, more preferably less than 5 ppm and even more preferably less than 1 ppm of polymerized material. Most preferably, the separated solvent and unreacted cyclic imino ether monomer comprises no polymerized material.

In the present method the cyclic imino ether monomer employed in the first and second reaction mixture can be the same or they can be different. Especially in case the separated unreacted cyclic imino ether monomer is utilized in the second reaction mixture, it is preferred to employ the same cyclic imino ether monomer in the first reaction mixture and the second reaction mixture.

In the method according to the present invention, the polymerization of the second reaction mixture is preferably carried out at relatively low temperatures. The reason for this is that at relatively low temperatures, the tautomerization of the cyclic imino ether to its enamine form is less favorable. It is important to keep the concentration of the enamine in the second reaction mixture as low as possible because it can cause chain transfer reactions during polymerization that increases heterogeneity of the molar mass of the resulting polymer chains as every chain transfer event leads to one terminated polymer chain and one newly initiated polymer chain.

Therefore, in the method according to the present invention, typically, the polymerization of the second reaction mixture is carried out at a temperature of not more than 60° C., preferably of not more than 50° C. The polymerization of the second reaction mixture is typically carried out at a temperature of at least 0° C., more preferably of at least 20° C. and most preferably of at least 30° C.

Typically, the second reaction mixture contains 10-95 wt. %, more preferably 20-80 wt. % and most preferably 20-50 wt. % of the cyclic imino ether monomer.

The solvent content of the second reaction mixture preferably lies in the range of 5-90 wt. %, more preferably of 20-80 wt. % and most preferably of 50-80 wt. %.

Polar, unreactive solvents were found to be the most suitable media for carrying out the polymerization of the second reaction mixture. Preferably, the solvent in the second reaction mixture is selected from optionally substituted aromatic hydrocarbons, sulfolane, dimethylacetamide and mixtures thereof. More preferably, said solvent is an optionally substituted aromatic hydrocarbon. Most preferably, the solvent is chlorobenzene.

The second reaction mixture preferably contains an initiator. More preferably, the second reaction mixture contains an initiator in a concentration of 0.00001-0.05 mol. %, even more preferably of 0.0005-0.01 mol. % calculated on the total amount of cyclic imino ether monomer present therein before the polymerization.

According to a particularly preferred embodiment the initiator used in the first and second reaction mixtures has a boiling point at ambient pressure of more than 150° C., more preferably of more than 200° C., most preferably or more than 250° C. The use of an initiator with a high boiling point offers the advantage that it remains in the second flask when cryogenically distilling the monomer and/or solvent from the first reactor into the second reactor.

The present method may also employ volatile initiators having a boiling point of less than 250° C. In case such volatile initiators are used, it is preferred to inject these volatile initiators into the first and/or second reaction mixture together with a liquid component (e.g. solvent).

According to a preferred embodiment of the method of the present invention, the initiator is a salt. Even more preferably, the initiator contained in the first and second reaction mixtures before polymerization is an oxazolinium salt. Most preferably, the oxazolinium salt is crystalline and is typically the adduct of a 2-substituted 2-oxazoline, such as 2-phenyl-2-oxazoline, and a strong acid (such as triflic, tetrafluroboric or hexafluorophoric) or alkylating agent.

The initiator employed in the method of the present invention in the first and/or second reaction mixtures may also include one or more functional initiators. A functional initiator is an initiator that contains a functional moiety and that is capable of introducing said functional moiety at the chain-end(s) of the polymer. Examples of functional initiators that may be employed include oxazolinium species prepared from a functional alkylating agent, such as propargyl triflate, oxazolinium species with a functionality in the 2-substituent of the oxazolinium, eg based on 2-methoxy-carboxyethyl-2-oxazoline or 2-(3-butenyl)-2-oxazoline, or a functional alkylating agent, such as propargyl triflate.

In a preferred embodiment of the method of the present invention, part of the total amount of cyclic imino ether monomer is reacted with chain breaking impurities in the first reaction mixture by sacrificial polymerization and the remaining amount of cyclic imino ether monomer is used in the second reaction mixture to produce the uniform polymer of high molar mass.

Accordingly, in the method of the present invention, it is preferred to employ the majority of the cyclic imino ether monomer in the second reaction mixture. Typically, the amount of cyclic imino ether monomer that is combined with the separated solvent represents at least 80 mol. %, more preferably at least 90 mol. % of the total amount of cyclic imino ether monomer that is employed in the method.

In the method according to the present invention, the polymerization reactions in the first and/or second reaction mixture may be terminated by an end-capping reaction of the living polymer with an appropriate nucleophilic terminating reagent. In a preferred embodiment, the polymerization in the second reaction mixture is end-capped with an appropriate terminating agent when the desired molecular weight is reached. The end-capping reaction thus enables the production of a well-defined polymer in terms of molecular weight and dispersity.

Examples of terminating reagents that may suitably be used to end-cap the high molar weight uniform polymer include: ammonia, sodium or potassium hydroxide in methanol, primary, secondary or tertiary amines (including piperidine and piperizine derivatives), thiols and phosphines.

The present method offers the advantage that it enables the manufacture of uniform polymers of high molar mass. Preferably, the uniform polymer obtained by the present method has a degree of polymerization of at least 200, more preferably of at least 250, even more preferably of at least 300 and most preferably of at least 400. Typically, the degree of polymerization of the uniform polymer does not exceed 10,000, more particularly it does not exceed 4,000, even more particularly it does not exceed 2,000.

Also in case of the present method dispersity of the uniform polymer tends to increase with increasing molecular mass. Typically, the uniform polymer obtained by the present method has degree of polymerization of 250 and a dispersity of less than $\theta_{max}$, wherein $\theta_{max}$ is calculated by the following equation (equation 1):

$\theta_{max}=1.2+(DP-250)/8000$ when $250 \leq DP<900$;

$\theta_{max}=1.28125+(DP-900)/500$ when $900 \leq DP<1000$;

$\theta_{max}=1.48125+(DP-1000)/9770$ when $1000 \leq DP$.

More preferably, the uniform polymer obtained by the present method has a dispersity of less than $\theta_{max}$, wherein θmax is calculated by the following equation (equation 2):

$\theta_{max}=1.15+(DP-250)/8000$ when $250 \leq DP<900$;

$\theta_{max}=1.23125+(DP-900)/500$ when $900 \leq DP<1000$;

$\theta_{max}=1.43125+(DP-1000)/9770$ when $1000 \leq DP$.

Most preferably, the uniform polymer obtained by the present method has a dispersity of less than $\theta_{max}$, wherein θmax is calculated by the following equation (equation):

$\theta_{max}=1.1+(DP-250)/8000$ when $250 \leq DP<900$;

$\theta_{max}=1.18125+(DP-900)/500$ when $900 \leq DP<1000$;

$\theta_{max}=1.38125+(DP-1000)/9770$ when $1000 \leq DP$.

In the following table $\theta_{max}$ values calculated for different $DP_{polymer}$ values by equations 1, 2 and 3 are listed.

| $DP_{polymer}$ | $\theta_{max}$ | | |
|---|---|---|---|
| | Equation 1 | Equation 2 | Equation 3 |
| 250 | 1.2 | 1.15 | 1.1 |
| 500 | 1.23125 | 1.18125 | 1.13125 |
| 900 | 1.28125 | 1.23125 | 1.18125 |
| 1,000 | 1.48125 | 1.43125 | 1.38125 |
| 4,000 | 1.78831 | 1.73831 | 1.68831 |

The uniform polymer obtained by the present method typically has a dispersity of less than 1.25, more preferably of less than 1.2 and even more preferably of less than 1.15, yet more preferably of less than 1.1 and most preferably of less than 1.08.

The dispersity of the polymers of the present invention can be determined by size exclusion chromatography using hexafluoroisopropanol with potassium trifluoroacetate (3 g/L) as eluent.

The method according to the present invention can be applied to produce homopolymers, block copolymers and statistical polymers.

Preferably, the uniform polymer produced by the present method is a homopolymer or a copolymer wherein at least 50%, more preferably at least 70% and most preferably at least 90% of the repeating units are derived from the cyclic imino ether monomer. Most preferably, the uniform polymer is a homopolymer or copolymer solely consisting of 2-oxazoline monomers.

The method according to the present invention can optionally comprise additional steps to functionalize the uniform polymer that is obtained by the polymerization of the second reaction mixture. For instance, functional moieties may be introduced in the structure of the polymer that enable it to form conjugates with an active moiety, such as a therapeutic moiety, a targeting moiety and/or a diagnostic moiety. These conjugates may suitably be used in the therapeutic treatment or prophylactic treatment or diagnosis of a disease or disorder.

The uniform polymer may also be functionalized by introducing electrophilic and/or nucleophilic moieties into pendant groups and/or the terminal end(s) of the polymer.

The introduction of these electrophilic and/or nucleophilic moieties enable the polymer to participate in crosslinking reactions with other functionalized polymers and/or with crosslinkers. The crosslinked materials thus obtained may suitably be applied as a material for various medical applications and devices, such as polymer conjugates and solid dispersions/solutions.

The method according to the present invention preferably yields a uniform polyoxazoline polymer as defined below.

Another aspect of the present invention concerns a polymer that is obtained by the polymerisation method described herein.

Yet another aspect of the present invention relates to a polyoxazoline polymer comprising at least 50 wt. %, more preferably at least 60 wt. % and most preferably at least 80 wt. % of repeating units derived from a 2-substituted 2-oxazoline monomer selected from 2-methyl-2-oxazoline, 2-ethyl-2-oxazoline, 2-n-propyl-2-oxazoline, 2-i-propyl-2-oxazoline and combinations thereof, said polymer having a DP of at least 250 and a dispersity of less than $\theta_{max}$, wherein $\theta_{max}$ is calculated by the following equation:

$\theta_{max}=1.2+(DP-250)/8000$ when $250 \leq DP<900$;

$\theta_{max}=1.28125+(DP-900)/500$ when $900 \leq DP<1000$;

$\theta_{max}=1.48125+(DP-1000)/9770$ when $1000 \leq DP$

More preferably, the polyoxazoline polymer has a dispersity of less than θmax, wherein $\theta_{max}$ is calculated by the following equation:

$\theta_{max}=1.15+(DP-250)/8000$ when $250 \leq DP<900$;

$\theta_{max}=1.23125+(DP-900)/500$ when $900 \leq DP<1000$;

$\theta_{max}=1.43125+(DP-1000)/9770$ when $1000 \leq DP$.

Most preferably, the polyoxazoline polymer has a dispersity of less than θmax, wherein $\theta_{max}$ is calculated by the following equation:

$\theta_{max}=1.1+(DP-250)/8000$ when $250 \leq DP<900$;

$\theta_{max}=1.18125+(DP-900)/500$ when $900 \leq DP<1000$;

$\theta_{max}=1.38125+(DP-1000)/9770$ when $1000 \leq DP$.

The polyoxazoline polymer of the present invention is preferably obtained by the polymerization method described herein.

The poloxazolyine polymer typically has a dispersity of less than 1.25, more preferably of less than 1.2, even more preferably of less than 1.15, yet more preferably of less than 1.1 and most preferably of less than 1.08.

According to a particularly preferred embodiment, the polyoxazoline polymer according to the present invention comprises at least 50 wt. %, most preferably at least 60 wt. % and most preferably at least 80 wt. % of repeating units derived from 2-ethyl-2-oxazoline.

In accordance with one embodiment of the invention the polyoxazoline polymer is a homopolymer, most preferably a homopolymer of 2-ethyl-2-oxazoline.

According to another embodiment of the invention, the polymer according to the present invention is a copolymer wherein at least 50%, preferably at least 60% and most preferably at least 80% of the repeating units are derived from 2-$C_{1-3}$-alkyl-2-oxazolines.

The polyoxazoline polymer according to the present invention is unique in that it combines a high degree of polymerization with a low (poly)dispersity.

According to a preferred embodiment, the polymer according to the present invention has a DP of at least 350, more preferably of at least 400.

The polyoxazoline polymer of the present invention may contain functional moieties in its structure that enable it to form conjugates with an active moiety, such as a therapeutic moiety, a targeting moiety and/or a diagnostic moiety. These conjugates of the polymer according to the present invention may consequently be used in the therapeutic treatment or prophylactic treatment or diagnosis of a disease or disorder.

The polyoxazoline polymer of the present invention may also contain electrophilic and/or nucleophilic moieties that enable it to crosslink with other polymers and/or with other crosslinkers. The crosslinked structures thus obtained may suitably be applied as a material for various medical applications and devices.

The polyoxazoline polymer of the present invention is preferably obtained by a method of producing a uniform polymer as defined herein before.

Yet another aspect of invention relates to pharmaceutical compositions or medical devices containing a polyoxazoline polymer as defined herein before. Examples of pharmaceutical compositions according to the present invention include polymer-conjugates with drugs, peptides or proteins, solid dispersions and solid solutions as well as other formulations with drugs, peptides or proteins.

Examples of medical devices that are encompassed by the present invention include tissue adhesive materials, hydrogel materials.

The invention is further illustrated by the following non-limiting examples.

EXAMPLES

Materials and Methods

2-Ethyl-2-oxazoline (EtOx) was fractionally distilled collecting a 128° C. boiling centre cut. It was then stirred over sodium for several days, degassed and distilled into a clean reservoir. 2-Methyl-2-oxazoline (MeOx) was purified in a similar manner.

2-Isopropyl-2-oxazoline and 2-n-propyl-2-oxazoline were synthesised via Witte-Seeliger cyclocondensation and purified as described for EtOx.

2-Methoxycarbonylethyl-2-oxazoline (MestOx) was synthesised via the one pot, two step reaction of the acid chloride and ethanolamine chloride, and was purified by distillation over barium oxide.

Chlorobenzene was washed three times with concentrated sulphuric acid (10% of volume being washed), three times with saturated aqueous sodium bicarbonate (10% of volume) and three times with water. It was dried over magnesium sulphate, filtered and then fractionally distilled and was then further dried by stirring with either phosphorous pentoxide or calcium hydride at least overnight before distillation.

Sulfolane was purified by the addition of potassium permanganate followed by methanol, filtration of manganese dioxide followed by fractional distillation. The fractionated sulfolane was distilled over calcium hydride, then phenyl oxazolinium tetrafluoroborate and handled inside a dry box.

Initiator salts were prepared by reacting freshly distilled 2-phenyl-2-oxazoline with an excess of the appropriate acid (triflic, tetrafluoroboric or hexaflurophosphoric) and recrystallizing the product at least once.

Polymerisation Procedure

A clean and dry distillation bridge was attached to a vacuum line via a cone socket, with a schlenk flask attached to one side and a three-way tap equipped round bottom flask on the other. Glass or Teflon coated stir bars had been placed on each side. The system was evacuated and backfilled with argon. Against a counterflow of argon 2-5 mL of trimethyl silyl chloride (TMSCl) was added via the tap on the schlenk flask and the system was isolated. The TMSCl was frozen by immersing the flask in liquid nitrogen and the system was evacuated. Upon thawing the TMSCl became the primary atmospheric component and reacted with the hydroxyl groups on the glass, rendering the system hydrophobic. After at least 30 minutes the system was purged with argon, the TMSCl was removed and the flasks were rinsed with water, acetone and petroleum ether before being dried on a stream of air.

Initiator (ca. 100 mg) was added to the schlenk flask to react with all chain breaking impurities (judged by the lack of colouration of the final reaction mixture). Another quantity of initiator was added to the receiving flask in which the main polymerisation was to be carried out, the quantity of which was dependent upon the desired polymer molar mass. The system was then evacuated for 16 hours.

To initiate the polymerisation, the system was purged with dry argon and solvent and monomer were injected into the schlenk flask and allowed to stir for one hour. The solution was then degassed three times via freeze-pump-thaw using liquid nitrogen for freezing technique and distilled into the polymerisation flask. After the polymerisation flask was thawed and purged with dry argon the flask was isolated by closing the three-way tap, disconnected from the vacuum line and placed in a preheated oil bath at 42-60° C.

To terminate the polymerisation, the flask was connected (via a butyl rubber hose) to a supply of dry argon, and (after withdrawing a small sample) a large excess of either potassium hydroxide (if a hydroxyl endgroup was desired) or ammonia (if an amine endgroup was desired) dissolved in methanol was added. The polymer was recovered by precipitation in diethyl ether followed by suction filtration (for higher MW polymers this was repeated 2-3 times to remove monomer and solvent which became kinetically trapped) and dried overnight in a vacuum oven or dessicator. The water-soluble polymers were then dissolved in water and lyophilised to obtain the final polymer product as a white powder.

Analysis of Polymers

Several different column systems were used to determine dispersity. The higher the resolution the narrower the polymer. In all cases the polymers were as narrow as the PMMA standards.

1. 2×PL HFIPGel and guard–low resolution, medium range (default unless noted otherwise)
2. 2×PSS PFG 100 Å and guard–high resolution, limited range (spec. 100-100,000 Da)
3. 2×PSS PFG Linear XL and guard–medium resolution and high range (spec. 100-3,000,000 Da)

Absolute MW was determined by viscometry for a series of synthesised polymers, and plotted against measured $M_p$ to derive a correction factor between PEtOx and the calibration standards (PMMA) of 0.777 in HFIP column set 1.

Dispersity was determined by size exclusion chromatography (SEC) using hexafluoroisopropanol with potassium trifluoroacetate (3 g/L) as eluent. Due to instrumental broadening caused by a very steep calibration curve (gradient=− 1.03167 min/log M) a comparative method was used to correct dispersity values, using the closest calibrant as comparator using the following equation:

$$\frac{\sigma^1}{\log Đ^1} = \frac{\sigma^2}{\log Đ^2}$$

Where σ=variance of the unknown (1) and calibrant (2), and $Đ^2$ is the reported dispersity of the calibrant.

Example 1

Poly(2-ethyl-2-oxazoline) of 40 kDa nominal weight bearing a terminal amine group was prepared by polymerization to near quantitative conversion.

A reaction system was charged with 121.9 mg H.PhOx.BF4 into the cleaning vessel and 57.9 mg (246 μmols) H.PhOx.BF4 in the polymerization vessel. Chlorobenzene (20 mL) and 2-ethyl-2-oxazoline (10 mL, 99 mmols, M:I ratio=403) was syringed into the cleaning vessel against a counterflow of dry argon. The reaction mixture turned yellow immediately upon the dissolution of the crystalline initiator. After one hour of stirring the liquids were degassed and statically distilled into the polymerization vessel and sealed, with no colour developing in the polymerization vessel. The polymerization vessel was heated to 42° C. for 21 days, and then (after sampling) terminated with 7 N ammonia in methanol (1 mL) before precipitation in diethyl ether yielding 8.75 g (89% yield) of a white polymer, being poly(2-ethyl-2-oxazoline) bearing an amine end-group.

Figure 1:
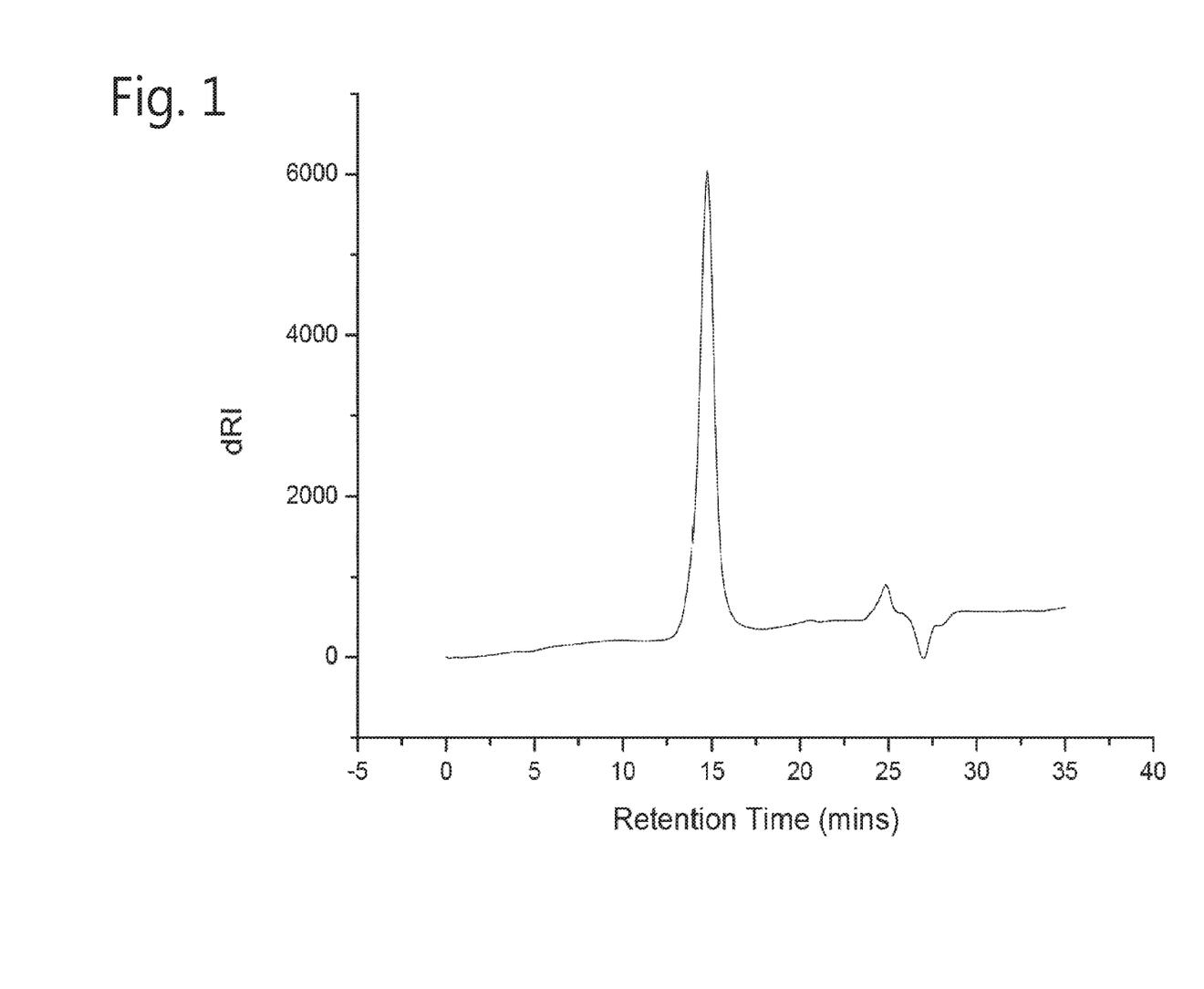

HFIP SEC revealed a monomodal peak as narrow as the PMMA standards used to calibrate the column as shown in FIG. 1.

SEC (eluent HFIP with KTFA): $M_p$=44,400 g/mol, $M_n$=46,100 g/mol, Đ=1.02

Example 2

A very high molecular weight (ca. 100 kDa) poly(2-ethyl-2-oxazoline) with a terminal amine was prepared as follows.

As per example 1, 95 mg H.PhOx.BF4 was placed in the cleaning vessel and 10.41 mg (44.3 μmols) in the polymerisation vessel. Chlorobenzene (20 mL) and 2-ethyl-2-oxazoline (10 mL, M:I=2,236) were added and the liquids handled as in Example 1. The polymerisation was regularly sampled and terminated at 74% conversion after 28 days at 42° C. Precipitation (3 rounds) yielded 5.10 g (70% yield) of a white polymer, being PEtOx bearing a terminal aminogroup.

Figure 2:
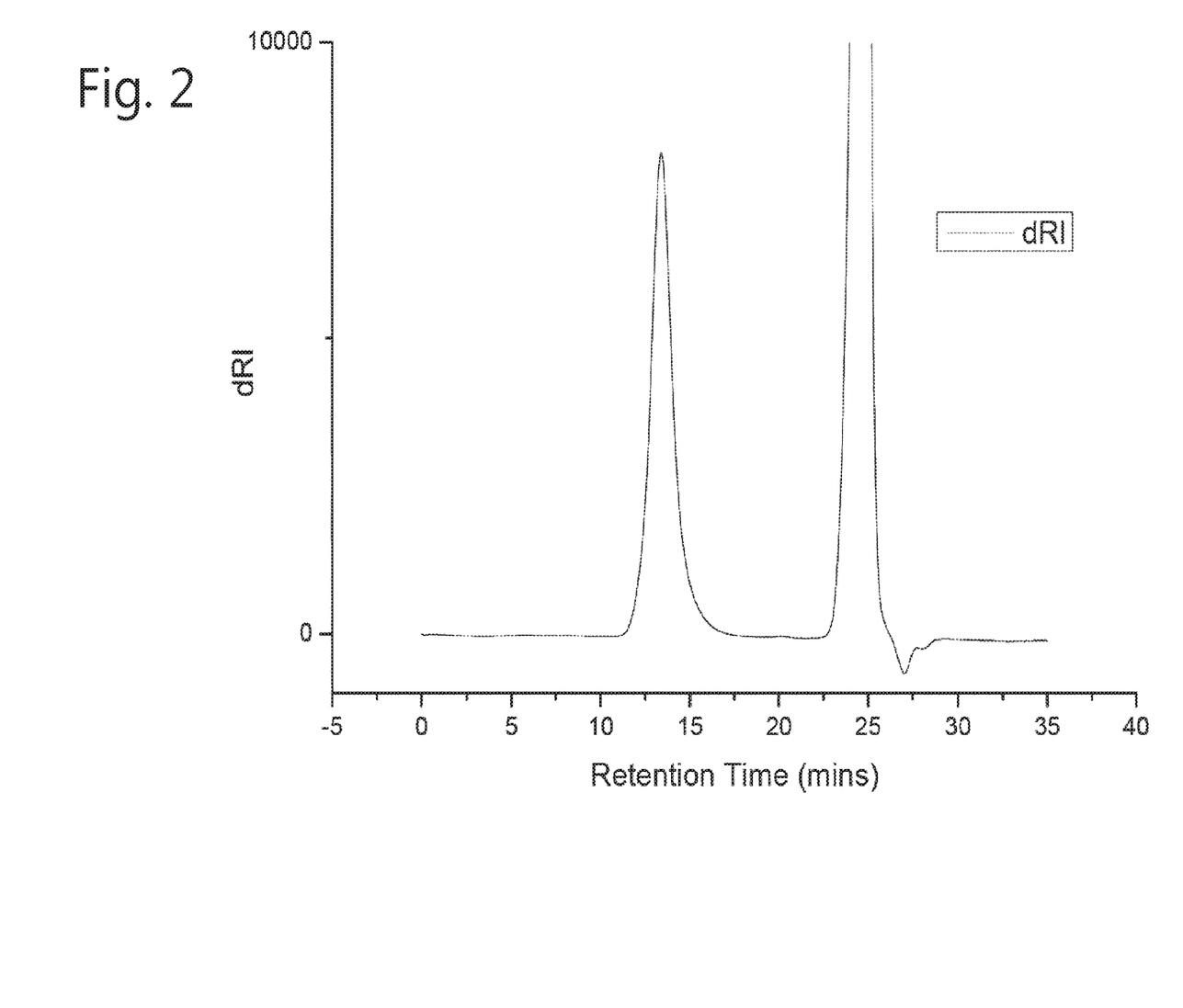

HFIP SEC revealed a monomodal peak as narrow as the PMMA standards used to calibrate the column as shown in FIG. 2.

SEC (eluent HFIP with KTFA): $M_p$=111,200 g/mol, $M_n$=94,100 g/mol, Đ=1.02

Example 3

Following the procedure of example 1, a series of PEtOx with different molecular masses was prepared and the results are summarized in Table 1. These were analysed by online viscometry and a correction factor of 0.777 was determined for HFIP. The eluting peaks in HFIP were truly poisson resembling the width of the PMMA standards.

| Nominal MW | $M_p$ (Universal Calibration) | $M_p$ (HFIP) | Đ (HFIP) |
|---|---|---|---|
| 10 kDa | 14,556 | 10,800 | 1.03 |
| 20 kDa | 21,308 | 18,600 | 1.03 |
| 30 kDa | 29,267 | 29,300 | 1.03 |
| 40 kDa | 43,899 | 44,400 | 1.02 |
| 50 kDa | 62,011 | 56,700 | 1.02 |
| 70 kDa | 66289 | 83,615 | 1.03 |
| 110 kDa | 106,286 | 143,042 | 1.02 |

Example 4

A block copoly(2-ethyl-2-oxazoline)(2-isopropyl-2-oxazoline) with a terminal amine group was prepared as follows.

As per previous examples 64.5 mg H.PhOx.BF4 was added to the cleaning vessel and 10.19 mg (43.4 μmols) to the polymerisation vessel. Chlorobenzene (5 mL) and 2-ethyl-2-oxazoline) (5 mL, M:I=1,141) were added and the liquids distilled into the polymerisation vessel and it was heated to 42° C. After 45 hours the reaction was sampled, and polymerisation vessel connected to the vacuum system, degassed and the liquids distilled out, followed by hard pumping. Chlorobenzene (15 mL) and 2-isopropyl-2-oxazoline (5 mL) were distilled in from 105.1 mg of H.PhOx.BF4, and the mixture was polymerisation at 42° C. for 110.75 hrs before termination with 7N ammonia in methanol (0.5 mL) and precipitation to yield 0.98 g of a white block copolymer.

Figure 3:
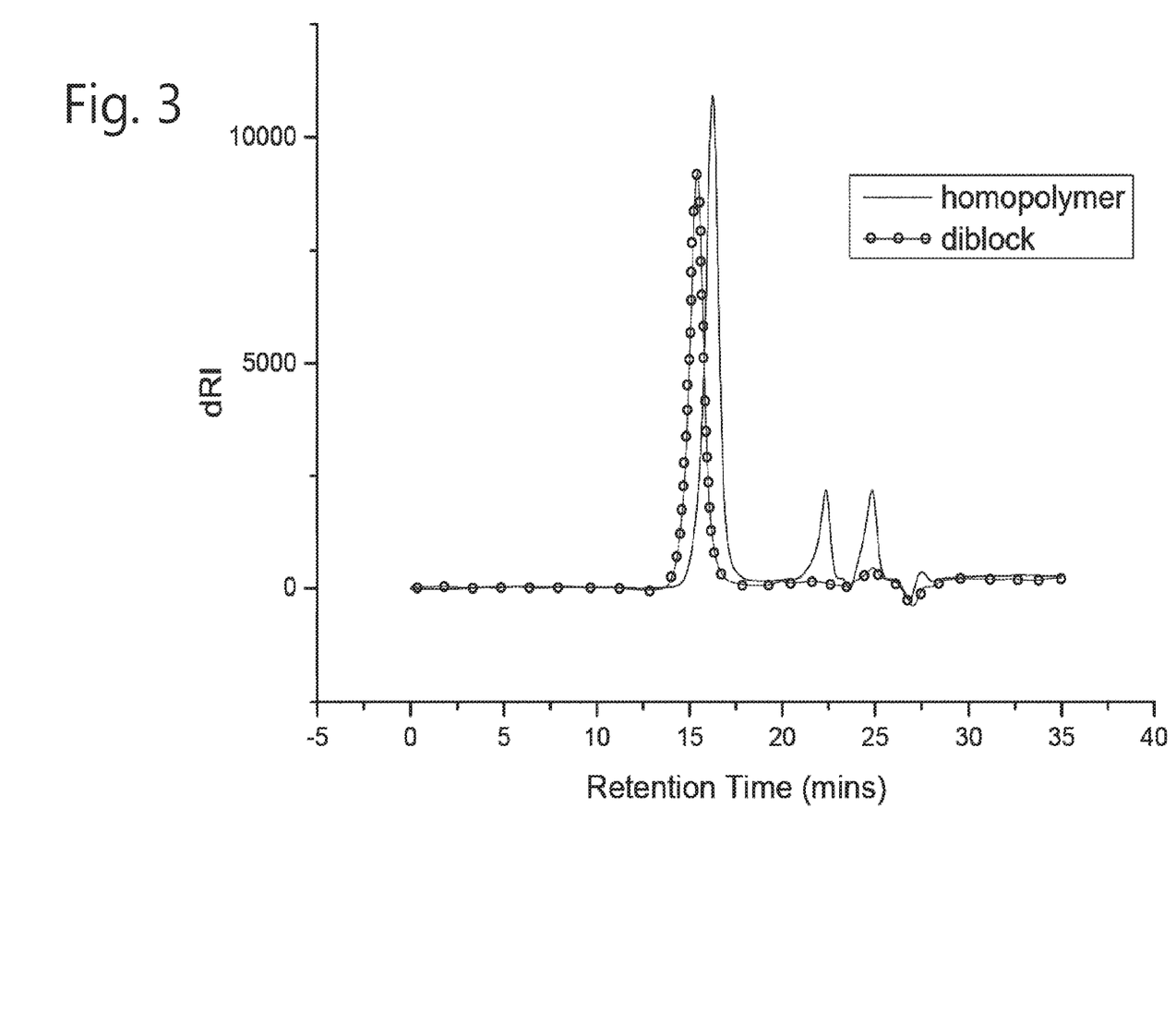

HFIP SEC revealed a monomodal peaks as narrow as the PMMA standards used to calibrate the column as shown in FIG. 3 for both the homopolymer and diblock copolymer.

SEC (eluent HFIP with KTFA): Monoblock: $M_p$=10,100 g/mol, $M_n$=10,100 g/mol, Đ=1.02, diblock: $M_p$=17,200 g/mol, $M_n$=16,900 g/mol, Đ=1.03.

Example 5

A statistical copolymer of 2-ethyl-2-oxazoline and 2-methoxycarboxyethyl-2-oxazoline (MestOx) with a terminal amine was prepared as follows.

As per previous examples, the cleaning vessel was charged with 96.4 mg H.PhOx.BF4 and the polymerization vessel with 11.14 mg (47.4 μmols). Chlorobenzene (10 mL), 2-ethyl-2-oxazoline (9 mL) and 2-methoxycarboxyethyl-2-oxazoline (1 mL, 1.16 g, 7.4 mmols) were added (feed ratio=1,881:152:1) and handled as described in the previous examples. After 12 days the reaction mixture was terminated as described in the previous examples and 2.783 g of a white powder which $^1$H-NMR revealed to by 13.1% MestOx and 82.9% EtOx.

Figure 4:
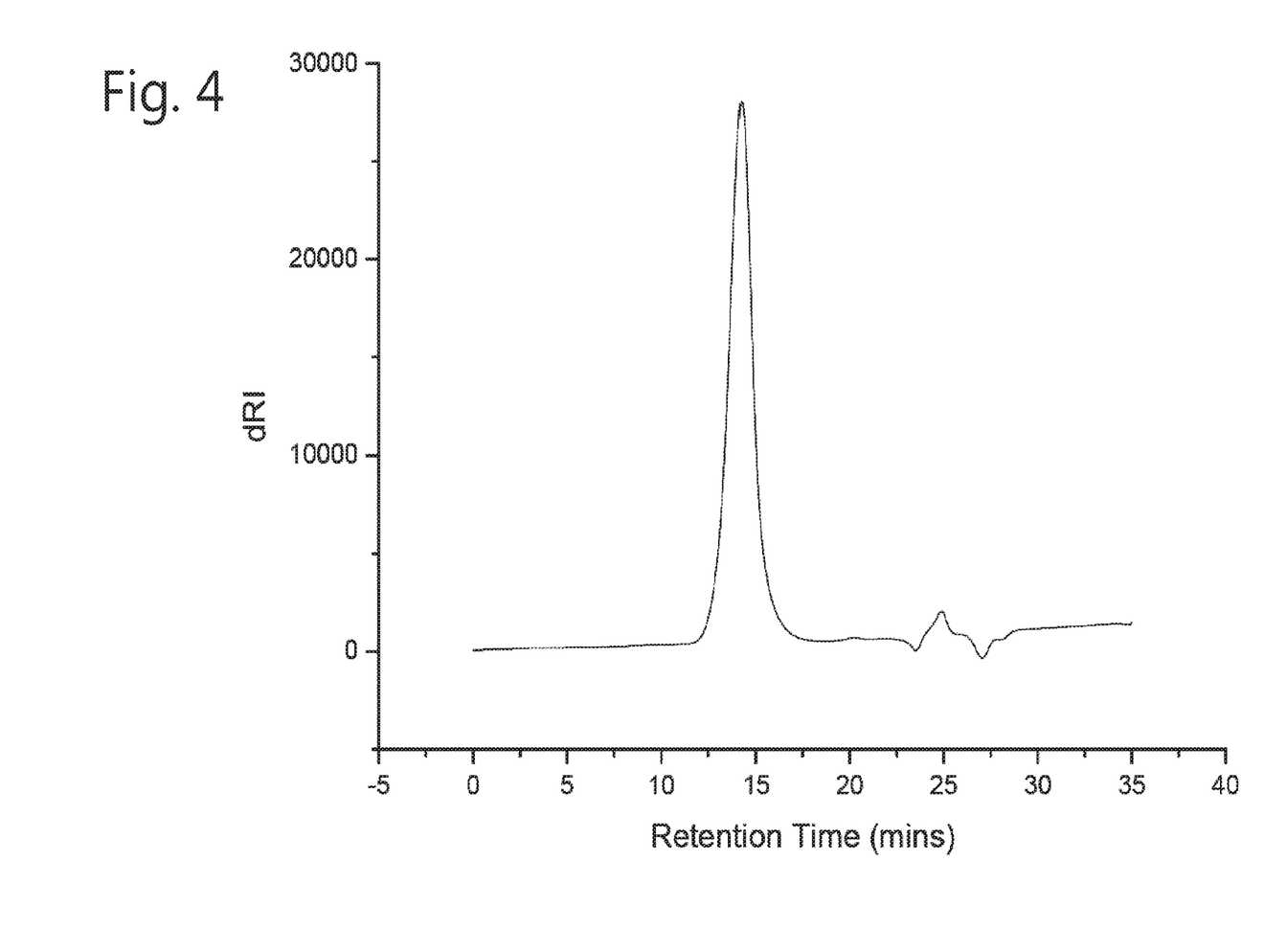

HFIP SEC revealed a monomodal peak as narrow as the PMMA standards used to calibrate the column as shown in FIG. 4.

SEC (eluent HFIP with KTFA): $M_p$=84,200 g/mol, $M_n$=74,200 g/mol, Đ=1.02

Example 6

A 100 kDa Poly(2-ethyl-2-oxazoline) bearing a terminal amine group was prepared at 60° C. as follows.

As per previous examples the cleaning vessel was charged with 114.0 mg H.PhOx.BF$_4$ and the polymerization vessel with 23.2 mg (98.7 μmols). Chlorobenzene (30 mL) and 2-ethyl-2-oxazoline (10.2 mL; M/I=1024) were added and handled as described in the previous examples. After 549 hours at 60° C. the reaction was terminated with an excess of methanolic ammonia. After precipitation into ether, dissolution in water and lyophilisation 8.8 g (91%) of a fluffy white powder was isolated.

Figure 5:
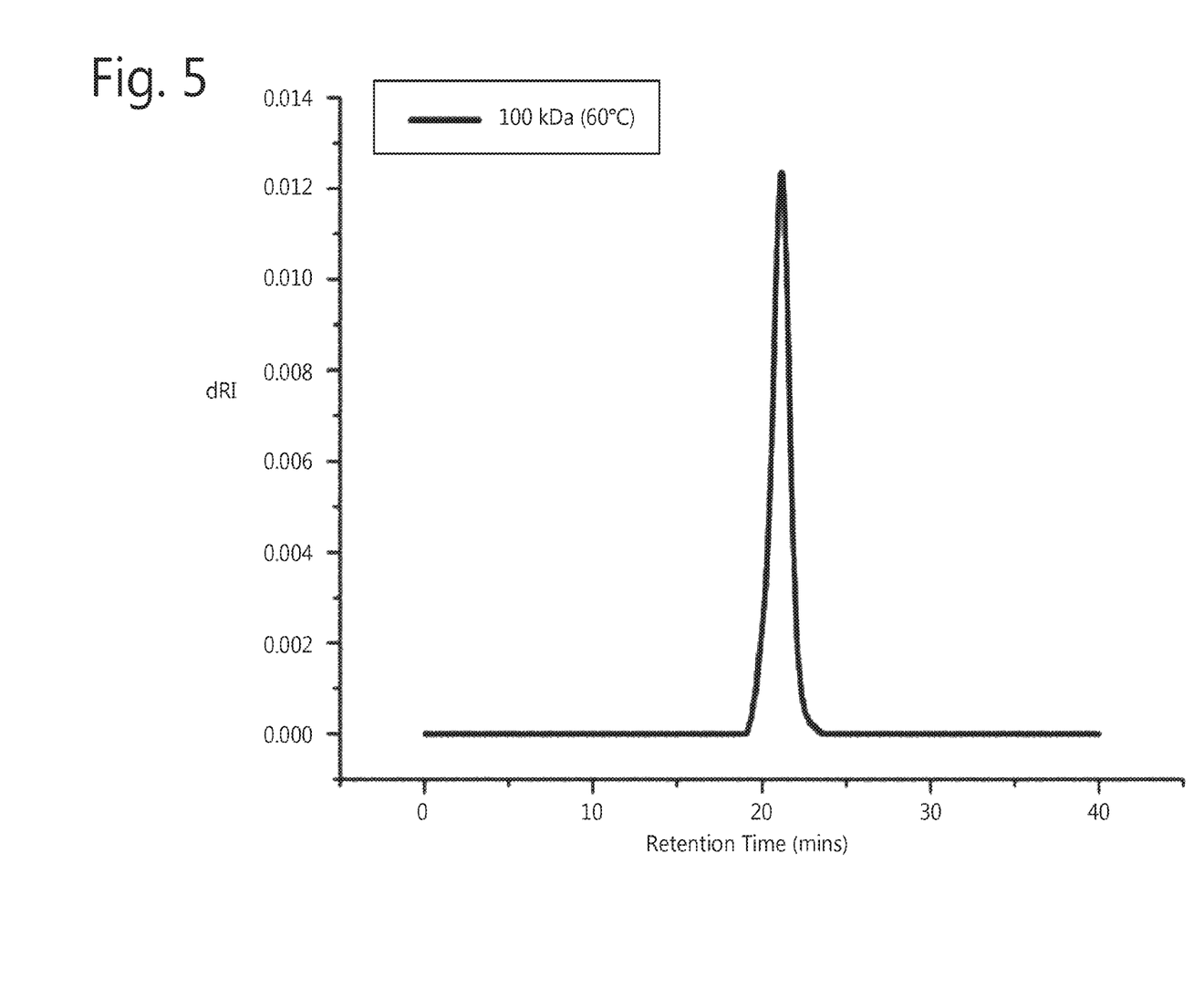

HFIP SEC revealed a monomodal peak as narrow as the PMMA standards used to calibrate the column as shown in FIG. 5.

SEC (eluent HFIP with KTFA, column set 3): $M_p$=111,100 g/mol uncorrected, Đ=1.10.

Example 7

A triblock poly(2-n-propyl-2-oxazoline)(2-ethyl-2-oxazoline)(2-n-propyl-2-oxazoline) copolymer was prepared as follows.

As per previous examples the cleaning vessel was charged with 92.4 mg H.PhOx.BF$_4$ and the polymerization vessel with 39.4 mg. 1,3 phenylene bisoxazolinium bistetrafluoroborate (100 μmol; a difunctional initiator). Chlorobenzene (20 mL) and 2-ethyl-2-oxazoline (10 mL; M/I=1010) were added and handled as in the previous examples. After 114.5 hours at 60° C. the reaction was sampled and the polymerisation vessel attached to the vacuum line and the volatiles removed by distillation and pumping. Chlorobenzene (20 mL) and 2-n-propyl-2-oxazoline (10 mL; 88.5 mmol) were distilled into the polymerization vessel and the polymerisation continued at 42° C. for 139.67 hours before termination with methanolic ammonia. After precipitation into ether, dissolution in water and lyophilisation 13.1 g of a fluffy white powder was isolated. $^1$H-NMR revealed the composition to be poly(nPrOx)$_{80}$(EtOx)$_{500}$(nPrOx)$_{80}$.

Figure 6:
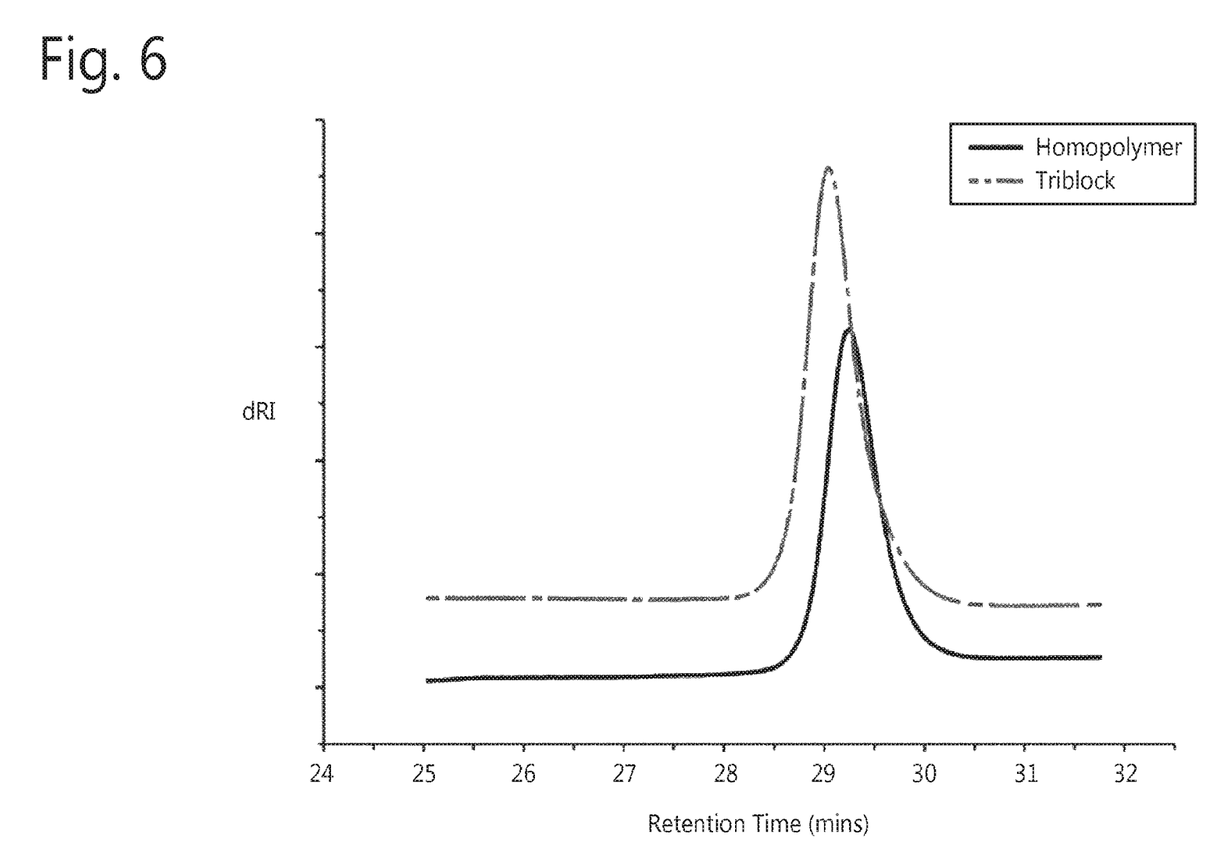

HFIP SEC revealed both the homopolymer and the triblock to have monomodal peaks as narrow as the PMMA standards used to calibrate the column as shown in FIG. 6.

SEC (HFIP with KTFA, column set 3) shows the first block to be $M_p$=106,200 g/mol (uncorrected), Đ=1.02 and the triblock to be $M_p$=143,600 g/mol (uncorrected), Đ=1.03.

Example 8

A 218 kDa Poly(2-ethyl-2-oxazoline) bearing a terminal amine was prepared at 60° C. as follows.

As per previous examples the cleaning vessel was charged with 75.6 mg H.PhOx.BF$_4$ and the polymerization vessel with 5.10 mg (21.7 μmols). Chlorobenzene (30 mL) and 2-ethyl-2-oxazoline (10.2 mL; M/I=4750) were injected as in the previous examples. After 672 hours at 60° C. (54% conversion) the reaction was terminated with an excess of methanolic ammonia. After precipitation into ether, dissolution in water and lyophilisation 4.63 g of a fluffy white powder was isolated.

Figure 7:
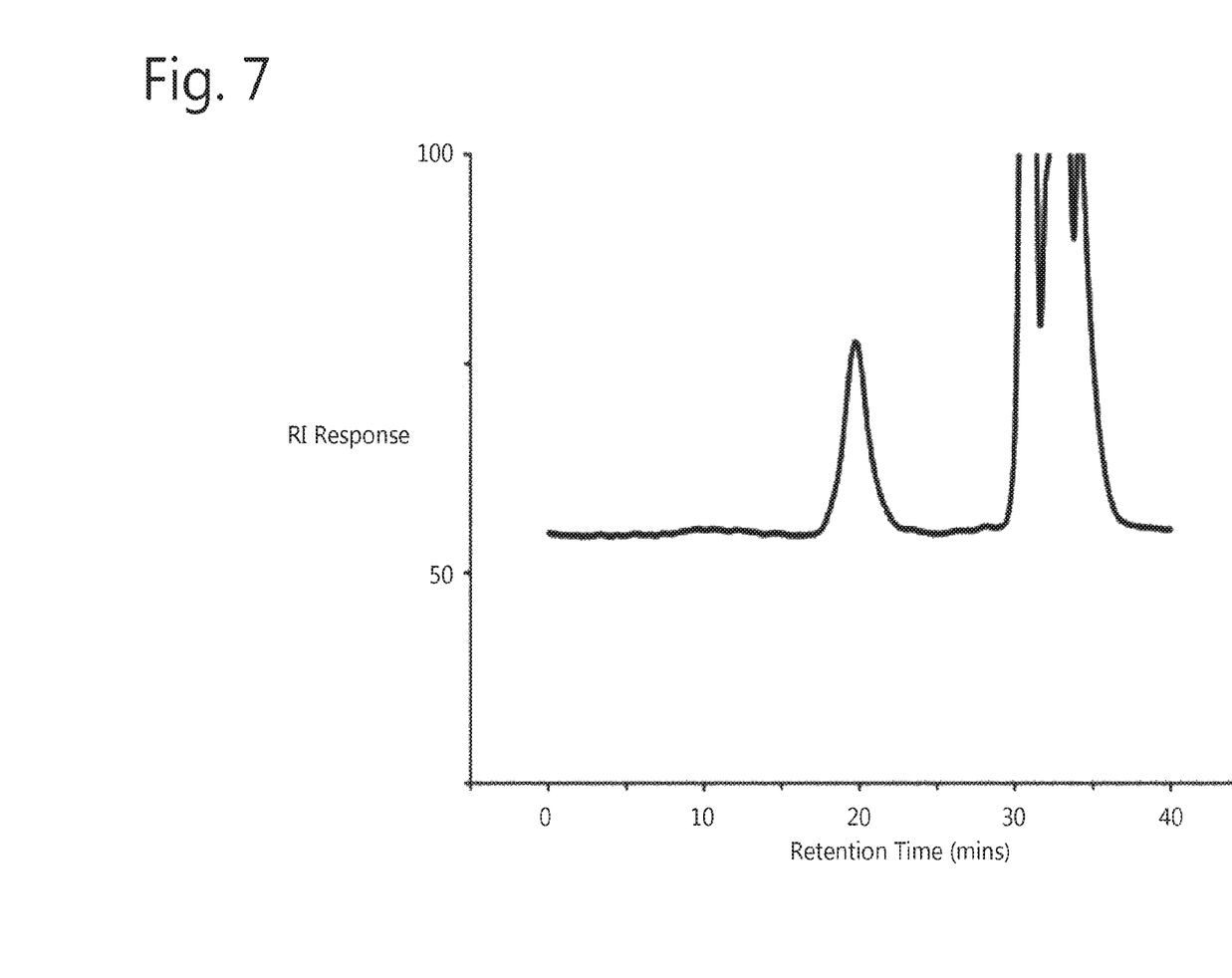

HFIP SEC revealed a monomodal peak as narrow as the PMMA standards used to calibrate the column as shown in FIG. 7.

SEC (HFIP with KTFA): $M_p$=218,000 g/mol corrected, Đ=1.02.

Example 9

A 10 kDa poly(2-n-propyl-2-oxazoline) was prepared as follows.

As per previous examples the cleaning vessel was charged with 185.0 mg H.PhOx.BF$_4$ and the polymerization vessel with 197.2 mg (0.84 mmols). Chlorobenzene (30 mL) and 2-ethyl-2-oxazoline (10.2 mL; M/I=107) were injected as in the previous examples. After 192 hours at 42° C. the reaction was terminated with an excess of methanolic ammonia. After precipitation into ether, dissolution in water and lyophilisation 9.5 g of a fluffy white powder was isolated.

Figure 8:
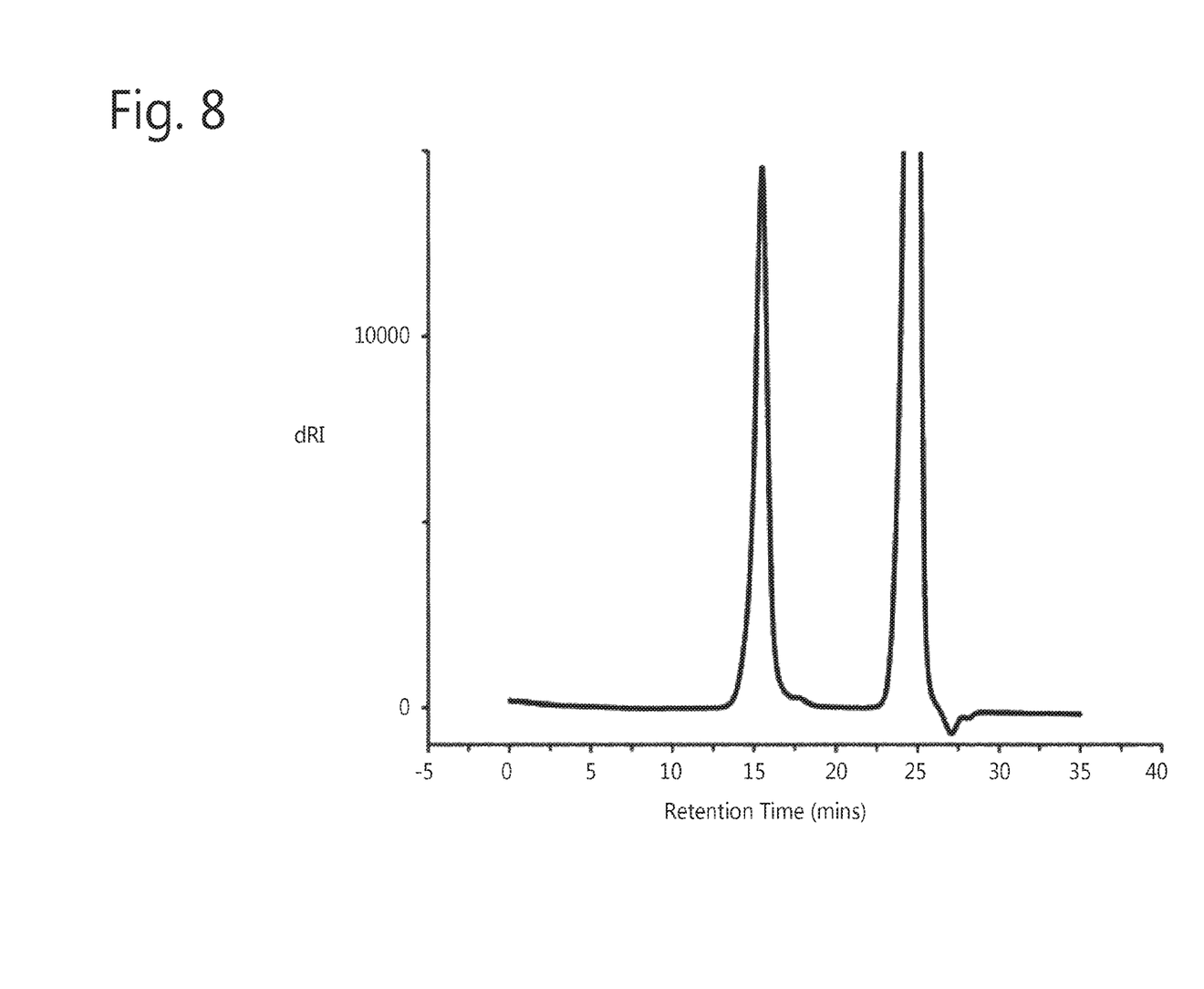

HFIP SEC revealed a monomodal peak as narrow as the PMMA standards used to calibrate the column as shown in FIG. 8.

SEC (HFIP with KTFA): $M_p$=13,200 g/mol corrected vs P(EtOx), Đ=1.02.

Example 10

A 50 kDa poly(2-methyl-2-oxazoline) bearing an amine endgroup was prepared as follows.

As per previous examples the cleaning vessel was charged with 12.0 mg H.PhOx.BF$_4$ and the polymerization vessel with 106.7 mg (0.45 mmols). 2-Methyl-2-oxazoline (25 mL; M/I=653) was injected as in the previous examples and distilled into the polymerisation vessel. Afterwards the polymerisation vessel was imported into a dry box and sulfolane (83.7 mL) added. After 216 hours at 60° C. the reaction was terminated with an excess of methanolic ammonia. After precipitation into ether, dissolution in water, dialysis and lyophilisation 15 g of a fluffy white powder was isolated.

Figure 9:
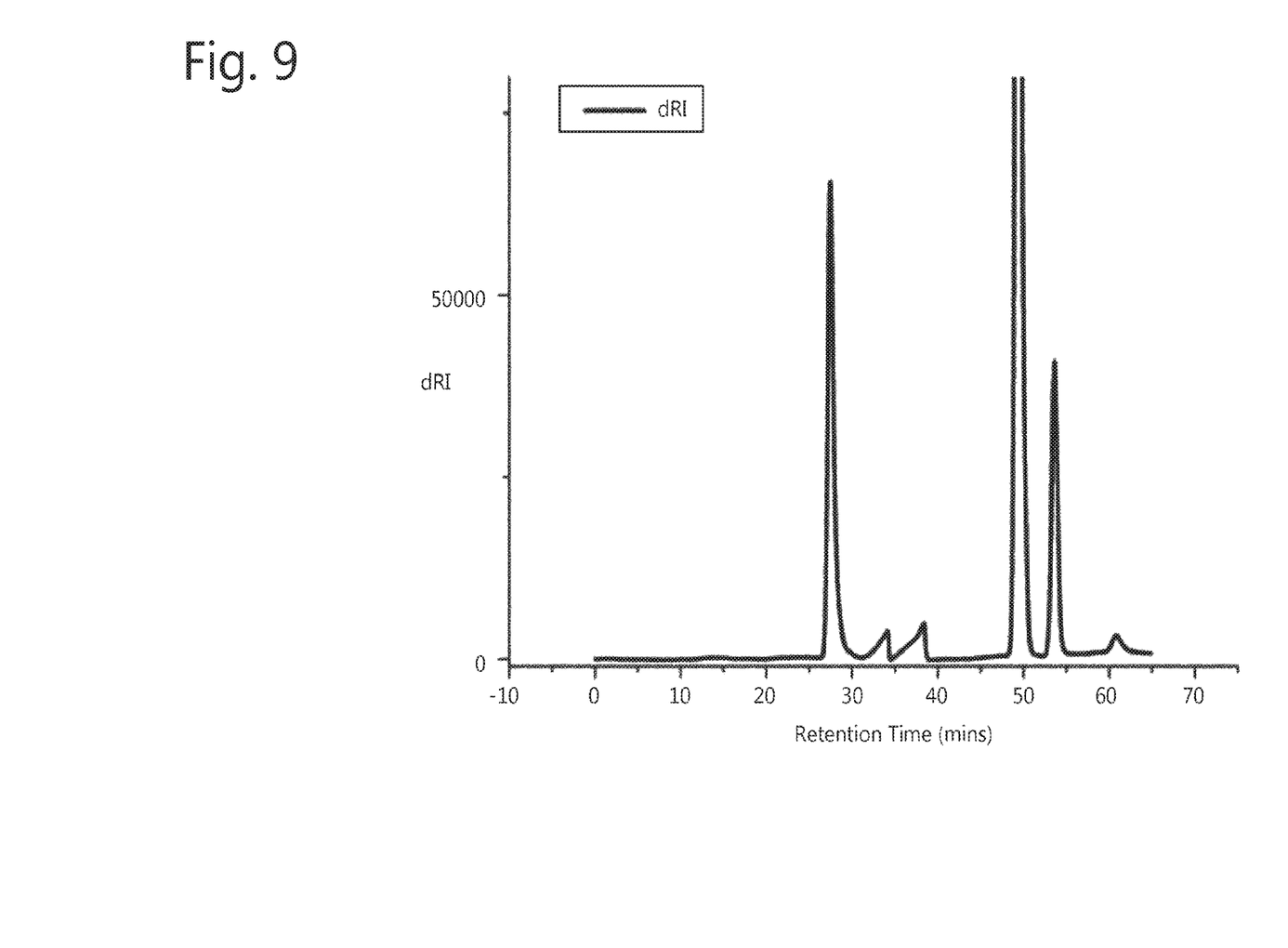

HFIP SEC revealed a monomodal peak as narrow as the PMMA standards used to calibrate the column as shown in FIG. 9.

SEC (HFIP with KTFA): $M_p$=104,800 g/mol uncorrected, Đ=1.11 uncorrected.

The invention claimed is:

1. A polyoxazoline polymer comprising at least 50 wt. % of repeating units derived from a 2-substituted 2-oxazoline monomer selected from 2-methyl-2-oxazoline, 2-ethyl-2-oxazoline, 2-n-propyl-2-oxazoline, 2-i-propyl-2-oxazoline and combinations thereof, said polymer having a degree of polymerisation (DP) of at least 400 and a dispersity of less than $Đ_{max}$, wherein $Đ_{max}$ is calculated by the following equation:

$Đ_{max}$=1.15+(DP−400)/8000 when 400≤DP<900;

$Đ_{max}$=1.23125+(DP−900)/500 when 900≤DP<1000;

$Đ_{max}$=1.43125+(DP−1000)/9770 when 1000≤DP.

2. The polymer according to claim 1, wherein the 2-substituted 2-oxazoline is 2-ethyl-oxazoline.

3. The polymer according to claim 1, wherein the polymer has a dispersity of less than 1.25.

4. The polymer according to claim 3, wherein the polymer has a dispersity of less than 1.2.

5. The polymer according to claim 1, wherein the polymer is obtained by a method comprising:
   a) providing a first liquid reaction mixture comprising a 2-substituted 2-oxazoline monomer selected from 2-methyl-2-oxazoline, 2-ethyl-2-oxazoline, 2-n-propyl-2-oxazoline, 2-i-propyl-2-oxazoline and combinations thereof and optionally solvent;
   b) polymerizing 2-substituted 2-oxazoline monomer in the first reaction mixture by cationic ring opening polymerization to produce a polymerized first reaction mixture containing (i) polymerized material and (ii) solvent and/or unreacted 2-substituted 2-oxazoline monomer;
   c) separating solvent and/or unreacted 2-oxazoline monomer from polymerized material contained in the polymerized first reaction mixture;
   d) providing a second liquid reaction mixture containing 2-substituted 2-oxazoline monomer and solvent by combining the separated unreacted 2-substituted 2-oxazoline monomer and/or the separated solvent with other components; and e) polymerizing the 2-substituted 2-oxazoline monomer in the second reaction mixture by cationic ring opening polymerization to produce a uniform polymer.

6. The polymer according to claim 5, wherein solvent and/or unreacted 2-substituted 2-oxazoline monomer is separated from polymerized material contained in the polymerized first reaction mixture by means of distillation.

7. A polymer comprising at least 50 wt. % of repeating units derived from a 2-substituted 2-oxazoline monomer selected from 2-methyl-2-oxazoline, 2-ethyl-2-oxazoline, 2-n-propyl-2-oxazoline, 2-i-propyl-2-oxazoline and combinations thereof, the polymer having a DP of at least 400 and a dispersity of less than $\theta_{max}$, wherein $\theta_{max}$ is calculated by the following equations:

$\theta_{max}=1.15+(DP-400)/8000$ when $400 \leq DP < 900$;

$\theta_{max}=1.23125+(DP-900)/500$ when $900 \leq DP < 1000$;

$\theta_{max}=1.43125+(DP-1000)/9770$ when $1000 \leq DP$, wherein the polymer is obtained by a method comprising the following steps:

a) providing a first liquid reaction mixture comprising a 2-substituted 2-oxazoline monomer selected from 2-methyl-2-oxazoline, 2-ethyl-2-oxazoline, 2-n-propyl-2-oxazoline, 2-i-propyl-2-oxazoline and combinations thereof and optionally solvent;

b) polymerizing 2-substituted 2-oxazoline monomer in the first reaction mixture by cationic ring opening polymerization to produce a polymerized first reaction mixture containing (i) polymerized material and (ii) solvent and/or unreacted 2-substituted 2-oxazoline monomer;

c) separating solvent and/or unreacted 2-substituted 2-oxazoline monomer from polymerized material contained in the polymerized first reaction mixture;

d) providing a second liquid reaction mixture containing 2-substituted 2-oxazoline monomer and solvent by combining the separated unreacted 2-substituted 2-oxazoline monomer and/or the separated solvent with other components; and e) polymerizing the 2-substituted 2-oxazoline monomer in the second reaction mixture by cationic ring opening polymerization to produce a uniform polymer.

8. A pharmaceutical composition or medical device comprising a polymer according to claim 1.

* * * * *